(12) United States Patent  
Melvin et al.

(10) Patent No.: US 7,419,794 B1
(45) Date of Patent: Sep. 2, 2008

(54) ANTIBODIES SPECIFIC FOR CYP1B1

(75) Inventors: William Melvin, Aberdeen (GB); Graeme Ian Murray, Aberdeen (GB)

(73) Assignee: University Court of the University of Aberdeen (GB)

( * ) Notice: Subject to any disclaimer, the term of this patent is extended or adjusted under 35 U.S.C. 154(b) by 0 days.

(21) Appl. No.: 09/936,979

(22) PCT Filed: Mar. 20, 2000

(86) PCT No.: PCT/GB00/01030

§ 371 (c)(1), (2), (4) Date: Jan. 24, 2002

(87) PCT Pub. No.: WO00/56773

PCT Pub. Date: Sep. 28, 2000

(30) Foreign Application Priority Data

Mar. 19, 1999 (GB) ................................. 9906380.2

(51) Int. Cl.
C07K 16/00 (2006.01)
C07P 21/08 (2006.01)
G01N 33/574 (2006.01)

(52) U.S. Cl. ................ 435/7.23; 530/387.9; 530/388.1; 530/388.8; 530/389.1; 530/391.3

(58) Field of Classification Search .............. 530/387.9, 530/388.1, 388.8, 388.85, 389.1, 389.7, 391.3; 435/7.23

See application file for complete search history.

(56) References Cited

U.S. PATENT DOCUMENTS 5,688,773 A * 11/1997 Chiocca et al. ................ 514/44
6,242,203 B1 * 6/2001 Melvin et al. ............... 435/7.23
6,824,780 B1 * 11/2004 Devaux et al. ............ 424/156.1

FOREIGN PATENT DOCUMENTS

WO WO 9007861 A1 * 7/1990
WO WO 97/12246 A 4/1997
WO WO 9712246 A1 * 4/1997

OTHER PUBLICATIONS

Pottenger et al. (Arch. Biochem. Biophys. 1991; 286: 488-497).*
Jain (Scientific American Jul. 1994).*
Dillman (Annals on Internal Medicine, vol. 111, pp. 592-603, 1989).*
Weiner (Seminars Oncology, vol. 26, No. 4, 1999, pp. 41-50).*
Gura (Science, v278, 1997, pp. 1041-1042).*
Kettleborough et al. (Protein Engineering 1991; 4: 773-783).*
Cambell, A.M. (Monoclonal Antibody Technology, Elsevier Science, NY, 1986, pp. 1-33).*
Bailey et al. (1998) "Association of cytochrome P450 1B1 (CYP1B1)polymorphism with steroid receptor status in breast cancer" *Cancer Research* 58(22):5038-41.
Bhattacharyya et al. (1995) "Identification of a Rat Adrenal Cytochrome P450 Active in Polycyclic Hydrocarbon Metabolism as Rat CYP1B1" *J. Biol. Chem.,* 270:11595-602.
Crespl et al. (1997) "Development of a human lyphoblastoid cell line constituitively expressing human CYP1B1 cDNA: substrate specificity with model substrates and promutagens" *Mutagenesis,* 12(2):83-9.
Duncan et al. (1992) "A simple enzyme linked immunosorbent assay (ELISA) for the neuron-specific γ isozyme of human enolase (NSE) using monoclonal antibodies raised against synthetic peptides corresponding to isozyme sequence differences." *J. Immunol. Meth.* 151:227-36.
Elston & Ellis (1991) "Pathelogical prognostic factors in breast cancer. I. The value of histological grade in breast cancer: experience from a large study with long-term follow-up." *Histopathology,* 19:403-410.
Hakkola et al. (1997) "Expression of CYP1B1 in human adult and fetal tissues and differential inducibility of CYP1B1 and CYP1A1 by Ah receptor ligands in human placenta and cultured cells." *Carinogensis* 18:391-97.
Hayes et al. (1996) "17 beta-estradiol hydroxylation catalyzed by human cytochrome P450 1B1" *PNAS, USA*93(18):9776-81.
King et al. (1997) "A highly senstive detection method for immunohistochemistry using biotinylated tyramine." *J. Pathol.* 183:237-41.
Liehr and Ricci (1996) "4-hydroxylation of estrogens as markers of human mammary tumors" *PNAS, USA* 93(8):3294-6.
McKay, J. et al. (1995) "Expression of cytochrome P450 CYP1B1 in breast cancer" *FEBS Letters*, 374:270-2.
Murray et al. (1997) "Tumor-specific expression of cytochrome P450 CYP1B1". *Cancer Research* 57:3026-31.
Murray et al. (1998) "Matrix metalloproteinase-1 is associated with poor prognosis in eosophageal cancer." *J. Pathol.* 185:256-61.
Murray et al. (1998) "Matrix metalloproteinases and their inhibitors in gastric cancer." *Gut,* 43:791-797.
Savas et al. (1994)"Mouse Cytochrome P-450EF, Representative of a New 1B Subfamily of Cytochrome P-450's" *J. Biol. Chem.* 269:14905-11.
Savas et al. (1997) "Biological Oxidation and P450 Reactions"*Arch. Biochem. Biophys.,* 347:181-92.
Schmidt & Bradfield (1996) "AH Receptor Signaling Pathways." *Annu. Rev. Cell Dev. Biol.* 12:55-89.
Shen et al. (1994) "cDNA Cloning, Sequence Analysis, and Induction by Aryl Hydrocarbons of aMurine Cytochrome P450 Gene, Cyb1b1." *DNA Cell Biol.* 13:763-9.
Shimada et al. (1996) "Activation of chemically diverse procarcinogens by human cytochrome P450 1B1" *Cancer Research* 56(13):2979-84.

(Continued)

*Primary Examiner*—Brandon J Fetterolf
(74) *Attorney, Agent, or Firm*—Quine Intellectual Property Law Group; Gary Baker

(57) ABSTRACT

Antibodies that can specially bind to cytochrome P450 CYP1B1 and methods of making them are disclosed, in particular antibodies that bind to amino acid sequence VNQWS-VNHDPVKWPN or PExFDPARFLDKDGy, where x is D or N and y is L or F, or an antigenic fragment thereof. The antibodies can be used in the diagnosis or treatment of cancers linked to enhanced CYP1B1 expression, including breast cancer, prostate cancer, colorectal cancer, liver cancer and ovarian cancer.

16 Claims, 4 Drawing Sheets

OTHER PUBLICATIONS

Sutter et al. (1994) "Complete cDNA Sequence of a Human Dioxin-inducible mRNA Identifies a New Gene Subfamily of Cytochrome P450 That Maps to Chromosome 2." *J. Biol.Chem.* 269:13092-9.

Tailor, G. et al. (1998) "Detection of cytochrome P450 CYP1B1 in human tumors using monoclonal antibodies against a c-terminal decapeptide" Human & Experimental Toxicology, vol. 17, No. 9, pp. 534. Proceedings of the British Toxicology Society Annual Congress Guilford, England, UK Apr. 19-22, 1998. *British Tocicological Society*, abstract.

Tang et al. (1996) "Isolation and Characterization of the Human Cytochrome P450 CYP1B1 Gene." *J. Biol. Chem.*, 271:28324-30.

Tang et al. (1999) "Development of an antipeptide antibody that binds to the C-terminal region of human CYP1B1" *Drug Metabolism and Disposition* (Feb. 1999) 27(2):274-80, abstract.

Walker et al. (1995) "Rat CYP1B1: an adrenal cytochrome P450 that exhibits sex-dependent expression in livers and kidneys of TCDD-treated animals." *Carcinogenesis*, 16:1319-27.

Wang et al. (1998) "Functional and physical interactions between the estrogen receptor Sp1 and nuclear aryl hydrocarbon receptor complexes." Nucl. Acid. Res. 26:3044-52.

\* cited by examiner 1 2 3 4

— 116
— 97

— 58

CYP1B1

CYP1B1

CYP1B1

SEQUENCE LISTING

```
<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 1

Val Asn Gln Trp Ser Val Asn His Asp Pro Val Lys Trp Pro Asn
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 2

Pro Glu Asp Phe Asp Pro Ala Arg Phe Leu Asp Lys Asp Gly Leu
 1               5                  10                  15
```

-continued

```
<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 3

Pro Glu Asp Phe Asp Pro Ala Arg Phe Leu Asp Lys Asp Gly Phe
 1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 4

Pro Glu Asn Phe Asp Pro Ala Arg Phe Leu Asp Lys Asp Gly Leu
 1               5                  10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 5

Pro Glu Asn Phe Asp Pro Ala Arg Phe Leu Asp Lys Asp Gly Phe
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 6

Asn Leu Pro Tyr Val Leu Ala Phe Leu Tyr Glu Ala Met Arg Phe
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 7

Ser Ser Phe Val Pro Val Thr Ile Pro His Ala Thr Thr Ala Asn
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 8

Thr Ser Val Leu Gly Tyr His Ile Pro Lys Asp Thr Val Val Phe
 1               5                  10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 9

Ile Asn Lys Asp Leu Thr Ser Arg Val Met Ile Phe Ser Val Gly
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 10

Lys Arg Arg Cys Ile Gly Glu Glu Leu Ser Lys Met Gln Leu Phe
 1               5                  10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 11

Leu Phe Ile Ser Ile Leu Ala His Gln Cys Asp Phe Arg Ala Asn
 1               5                  10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 12

Pro Asn Glu Pro Ala Lys Met Asn Phe Ser Tyr Gly Leu Thr
 1               5                  10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 13

Ile Lys Pro Lys Ser Phe Lys Val Asn Val Thr Leu Arg Glu
 1               5                  10
```

ANTIBODIES SPECIFIC FOR CYP1B1

CROSS-REFERENCE TO RELATED APPLICATIONS

This application is a national stage application filed under 35 U.S.C. § 371 and claim priority to and benefit of a prior international application number PCT/GB00/01030, Antibodies Specific for CYP1B1, by William Melvin, et al., filed Mar. 20, 2000, which claims priority to United Kingdom application 9906380.2, filed Mar. 19, 1999. The full disclosure of the prior applications are incorporated herein by reference.

FIELD OF THE INVENTION

The present invention relates to tumour diagnosis and therapy, and in particular to antibodies specific for tumour specific cytochrome P450 CYP1B1.

BACKGROUND OF THE INVENTION

Cytochrome P450 (P450) CYP1B1 is the only known member of a recently identified sub-family of the CYP1 gene family. Human CYP1B1 was originally isolated from a dioxin treated keratinocyte cell line (Sutter et al., 1994) as part of a series of investigations to identify differential expression of genes caused by exposure to dioxin. The human CYP1B1 gene is located on chromosome 2p22-21 spanning 12 kb and is composed of three exons and two introns (Tang et al., 1996). The mRNA is 5.2 kb and encodes for a protein of 543 amino acids (Sutter et al., 1994). This is the largest known human P450 gene both in terms of mRNA size and number of amino acids and is also the simplest structurally. Both nucleic acid and amino acid sequence analysis shows that CYP1B1 displays only approximately 40% homology with CYP1A1 and CYP1A2. The low degree of similarity with existing members of the CYP1 family resulted in this P450 being assigned to a new CYP1 sub-family CYP1B which to date only contains the single member CYP1B1. Indeed hybridisation studies of human DNA suggests that there is only one member of the CYP1B gene family (Sutter et al., 1994). The CYP1B1 gene is transcriptionally activated by ligands of the Ah receptor including planar aromatic hydrocarbons (Sutter et al., 1994, Hakkola et al., 1997) and the most potent of these Ah receptor agonists for inducing transcription of the CYP1B1 gene appears to be dioxin (Hakkola et al., 1997).

Orthologous forms of this P450 have also recently been isolated from a benzanthracene-induced cell line derived from mouse embryo fibroblasts (Savas et al., 1994; Shen et al., 1994) and adult rat adrenal cortex (Bhattacharyya et al., 1995; Walker et al., 1995). Although there is a high degree (greater than 80%) of both nucleic acid and amino acid sequence homology between the human, mouse and rat forms of CYP1B1 there also appears to be considerable species differences regarding tissue specific expression, regulation and metabolic specificity of CYP1B1 (Savas et al., 1994; Sutter et al., 1994; Bhattacharyya et al., 1995; Savas et al., 1997).

Breast cancer is the commonest cancer to affect women and is an estrogen dependent tumour. Human CYP1B1 expressed in yeast (S. cerevisiae) shows high specific activity towards the 4-hydroxylation of 17β-estradiol (Hayes et al., 1996) converting it to 4-hydroxyestradiol and indeed human CYP1B1 is considered to be the most efficient 4-hydroxylase of 17β-estradiol. In contrast mouse CYP1B1 does not appear to act as an estradiol hydroxylase (Savas et al., 1997) indicating species differences in the metabolic capability of CYP1B1. Liehr and Ricci (1996) showed that there is a significant level of 4-hydroxylation of 17β-estradiol in breast cancer microsomes. They showed considerably higher 4-hydroxylation of 17β-estradiol in microsomes prepared from breast cancer compared with only a very low level of 4-hydroxylation present in normal breast tissue. Both immunoreactive CYP1B1 protein (Murray et al., 1997) and CYP1B1 mRNA (McKay et al., 1995) have been identified in breast cancer indicating that CYP1B1 is a major form of cytochrome P450 expressed in breast cancer.

SUMMARY OF THE INVENTION

The initial immunohistochemical studies of CYP1B1 in Murray et al. (1997) showed enhanced CYP1B1 expression in several types of human cancer including breast cancer and were performed using a polyclonal antibody to CYP1B1. The present invention relates to further developments in this area and concerns further antibodies specific for human CYP1B1, and in particular monoclonal antibodies raised using synthetic peptides based on CYP1B1 amino acid sequence as immunogens. The work described herein discloses the uses of the antibodies in immunohistochemistry and in the investigation of the expression of CYP1B1 by immunohistochemistry in a series of primary human breast cancers.

Accordingly, in a first aspect, the present invention provides a method of making an antibody that specifically binds to cytochrome P450 CYP1B1, the method comprising raising the antibody using a peptide consisting of an amino acid sequence VNQWSVNHDPVKWPN (SEQ ID NO. 1) or PExFDPARFLDKDGy, where x is D or N and y is L or F (SEQ ID NOs. 2 to 5), or an antigenic fragment thereof.

Typically, the antigenic fragments within these peptide sequences consist of 3 to 10 amino acids and more typically 3 to 6 amino acids.

In a further aspect, the present invention provides a method of producing an antibody having obtained a hybridoma by the above method, the method comprising culturing a hybridoma producing the antibody and isolating the antibody thus produced. The method may comprise the further step of conjugating the antibody to an effector moiety such as a label, a toxin, a drug or a transport molecule.

In a further aspect, the present invention provides an antibody which is capable of specifically binding to cytochrome P450 CYP1B1, wherein the antibody recognises an epitope in the cytochrome P450 CYP1B1 protein included within the amino acid sequence VNQWSVNHDPVKWPN (SEQ ID NO. 1) or PExFDPARFLDKDGy, where x is D or N and y is L or F (SEQ ID NOs. 2 to 5).

Preferably, the antibody recognises an epitope of between 3 and 10 amino acids from the amino acid sequences, and more preferably an epitope of between 3 and 6 amino acids from the amino acid sequences.

Preferred antibodies are monoclonal antibodies, for example as obtainable by:
 (a) immunising an animal with the peptide conjugated to an immunogenic carrier;
 (b) sacrificing the animal and fusing spleen cells obtained from the animal with myeloma cells to produce one or more hydridomas; and,
 (c) screening the hybridomas for antibodies capable of binding the peptide.

The antibodies may be conjugated to an effector, such a label, a toxin, a drug or prodrug, an enzyme or a transport molecule.

In a further aspect, the present invention provides the above antibodies for use in a method of medical treatment.

In a further aspect, the present invention provides the use of these antibodies for the preparation of a medicament for the treatment of cancer.

In a further aspect, the present invention provides a peptide consisting essentially of amino acid sequence VNQWSVN-HDPVKWPN (SEQ ID NO. 1) or PExFDPARFLDKDGy wherein x is D or N and y is L or F (SEQ ID NOs. 2 to 5).

In a further aspect, the present invention provides an assay method for detecting cancer cells present in a sample from a patient, the method comprising contacting a tissue sample from a patient with one of the above antibodies, and detecting binding of the antibody to CYP1B1 protein present in the sample as an indication of the presence of cancer cells in the tissue sample.

By way of example, the step of detecting the binding of the antibody to CYP1B1 protein is carried out using an antibody capture assay, a two-antibody sandwich assay or an antigen capture assay.

Preferably, the method is used to assist in the diagnosis or prognosis of breast cancer, colorectal cancer, prostate cancer, liver cancer or ovarian cancer.

Various further aspects and embodiments of the present invention will be apparent to those skilled in the art in view of the present disclosure. Certain aspects and embodiments of the invention will now be illustrated by way of example and with reference to the following figures.

BRIEF DESCRIPTION OF THE FIGURES

FIG. 1: Immunoblot of expressed CYP1B1 with monoclonal antibody (5D3) demonstrating specificity for CYP1B1. Lane 1, expressed CYP1B1 (10 µg of microsomal protein, 0.86 pmol of CYP1B1); lane 2, expressed CYP1A1 (10 µg of microsomal protein, 0.53 pmol of CYP1A1); lane 3, control lymphoblastoid microsomes containing only vector (10 µg of microsomal protein) and lane 4, normal human liver microsomes (10 µg of microsomal protein). Molecular weight markers are shown on the right in kiloDaltons.

FIG. 2: Immunoblot demonstrating the minimum detectable amount of CYP1B using monoclonal antibody 5D3. Lane 1 to lane 6 decreasing amounts of expressed CYP1B1. Lane 1, 0.86 pmol of CYP1B1; lane 2, 0.43 pmol of CYP1B1; lane 3, 0.21 pmol of CYP1B1; lane 4, 0.1 pmol CYP1B1; lane 5, 0.05 pmol of CYP1B1 and lane 6, 0.025 pmol of CYP1B1. Molecular weight markers are shown on the right in kiloDaltons.

FIG. 3: Immunoblot of CYP1B1 of microsomes prepared from various normal human tissues. Lane 1, expressed CYP1B1 (10 µg of microsomal protein corresponding to 0.86 pmol of CYP1B1); lane 2, liver; lane 3, kidney; lane 4, lung; lane 5, pancreas; lane 6, adrenal cortex; lane 7, brain (medulla); lane 8, stomach; lane 9, jejunum; lane 10, colon; lane 11, breast and lane 12, ovary (30 µg of microsomal protein loaded per lane of normal human tissue). Molecular weight markers are shown on the right in kiloDaltons.

DETAILED DESCRIPTION

Antibodies

Figure 4:
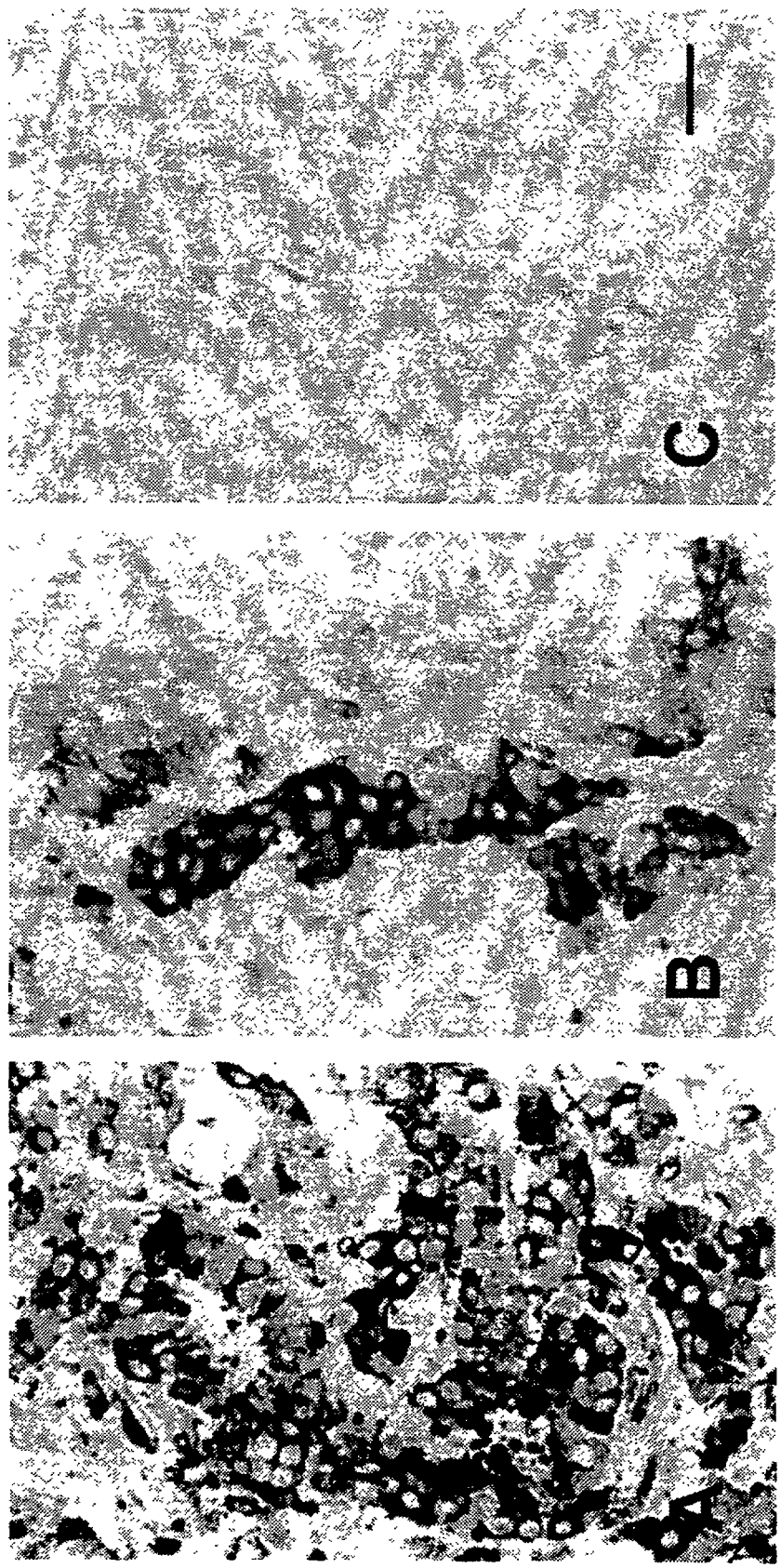
FIG. 4: Immunohistochemical demonstration of CYP1B1 in breast cancer using monoclonal antibody 5D3, A. Localisation of CYP1B1 in a grade 3 invasive ductal carcinoma. There is strong immunoreactivity for CYP1B1 in tumour cells, B. localisation of CYP1B1 in an invasive lobular carcinoma demonstrating strong immunoreactivity in breast cancer cells and C. There is no immunoreactivity in a grade 3 invasive ductal carcinoma when the primary CYP1B1 monoclonal antibody is replaced by TBS in the immunohistochemical procedure. Scale bar represents 60 µm.

Based on the description provided herein the skilled person can obtain further antibodies which are capable of specifically binding CYP1B1 using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature 357:80-82, 1992). Isolation of antibodies and/or antibody-producing cells from an animal may be accompanied by a step of sacrificing the animal.

As an alternative or supplement to immunising a mammal with a peptide as shown in the examples, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

In the present application, the term "antibody" is defined as covering any binding substance having a binding domain with the required specificity, namely the property of specifically binding to CYP1B1, and which preferably does not substantially bind to related proteins such as CYP1A1 and CYP1A2, which share approximately 40% homology with CYP1B1, or to unrelated proteins. The term "antibody" includes antibody fragments, derivatives, functional equivalents and homologues of antibodies, including synthetic molecules and molecules whose shape mimics that of an antibody enabling it to bind an antigen or epitope. Preferably, the antibodies bind to an epitope within the amino acid sequences of peptide D or E, such epitopes consisting of between 3 and 10, and more preferably between 3 and 6 amino acids. Preferred antibodies bind to CYP1B1 with a binding affinity of greater $10^{-6}$, more preferably greater than $10^{-8}$ $mol^{-1}$, as determined by Scatchard analysis (see Antibodies, A Laboratory Manual, eds Harlow and Lane, Cold Spring Harbor, 1988).

Examples of antibody fragments which are capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

In one embodiment, the antibodies of the invention are humanised. Humanised forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanised antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanised antibodies may also comprise residues which are found neither in the recipient antibody nor in the imported CDR or framework sequences. In general, the humanised antibody will comprise substantially all of at least one, and typically two, variable domains, in which all or substantially all of the CDR regions correspond to those of a non-human immunoglobulin and all or substantially all of the FR regions are those of a human Immunoglobulin consensus sequence. The humanised antibody optimally also will comprise at least a portion of an immunoglobulin constant region (Fc), typically that of a human immunoglobulin. see for example Jones et al., Nature, 321:522-525, 1986; Riechmann et al., Nature, 332: 323-329, 1988; and Presta, Curr Op Struct. Biol., 2:593-596, 1992.

Methods for humanising non-human antibodies are well known in the art. Generally a humanised antibody has one or more amino acid residues introduced into it from a source which is non-human. These non-human amino acid residues are often referred to as "import" residues, which are typically taken from an "import" variable domain. Humanisation can be essentially performed following the method disclosed in Jones et al., Nature, 321:522-525, 1986; Riechmann et al., Nature, 332:323-327, 1988; Verhoeyen et al., Science, 239: 1534-1536, 1988, by substituting rodent CDRs or CDR sequences for the corresponding sequences of a human antibody. Accordingly, such "humanised" antibodies are chimeric antibodies (U.S. Pat. No. 4,816,567), wherein substantially less than an intact human variable domain has been substituted by the corresponding sequence from a non human species. In practice, humanised antibodies are typically human antibodies in which some CDR residues and possibly some FR residues are substituted by residues from analogous sites in rodent antibodies.

Bispecific antibodies are monoclonal, preferably human or humanised, antibodies that have binding specificities for at least two different antigens. In the present case, one of the binding specificities is for the CYP1B1, the other one is for any other antigen. Methods for making bispecific antibodies are known in the art. Traditionally, the recombinant production of bispecific antibodies is based) on the co-expression of two immunoglobulin heavy-chain/light-chain pairs, where the two heavy chains have different specificities, see Milstein and Cuello, Nature, 305:537-539, 1983. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The antibodies of the invention can be coupled or conjugated to an effector moiety such as a label, a toxin, a drug or a transport molecule, using techniques well known in the art. For diagnostic uses the antibodies are typically linked to a label. The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

Assays

Methods for determining the presence or amount of a marker such as CYP1B1 in a sample from an individual are well known in the art and readily adapted by the skilled person to employ the antibodies disclosed herein as binding agents and/or developing agents, e.g. to assist in determining the presence or amount of CYP1B1 in an assay. The results of such assays can in turn allow a physician to determine whether a patient suffers from a condition or is at risk of developing a condition associated with CYP1B1 expression (either over expression or under expression), such as cancer. The results of the assay can in turn allow the physician to optimise the treatment of the conditions, providing appropriate therapeutic and/or prophylactic treatment, permitting stream-lining of treatment by targeting those most likely to benefit.

In preferred embodiments, the presence or amount of CYP1B1 is used in the diagnosis of cancer, and especially breast cancer, prostate cancer, colorectal cancer, liver cancer or ovarian cancer.

The methods typically employ a biological sample from patient such as blood, serum, tissue, serum, urine or other suitable body fluids. A preferred patient sample is tissue selected from bladder, brain, breast, colon, connective tissue, kidney, lung, lymph node, oesophagus, ovary, skin, stomach, testis and uterus.

The antibodies can be used as binding agents as they have binding sites capable of specifically binding to CYP1B1 in preference to other molecules. In some formats of assay, the binding agents are immobilised on solid support, e.g. at defined, spatially separated locations, to make them easy to manipulate during the assay. The sample is generally contacted with the binding agent(s) under appropriate conditions which allow the analyte in the sample to bind to the binding agent(s). The fractional occupancy of the binding sites of the binding agent(s) can then be determined either by directly or indirectly labelling the analyte or by using a developing agent or agents to arrive at an indication of the presence or amount of the analyte in the sample.

In other embodiments, the antibodies of the invention can be used as developing agents to detect CYP1B1 in biological samples by directly or indirectly labelling the antibodies, e.g. with radioactive, fluorescent or enzyme labels, such as horseradish peroxidase) so that they can be detected using techniques well known in the art. Directly labelled developing agents have a label associated with or coupled to the agent. Indirectly labelled developing agents may be capable of binding to a labelled species (e.g. a labelled antibody capable of binding to the developing agent) or may act on a further species to produce a detectable result. Thus, radioactive labels can be detected using a scintillation counter or other radiation counting device, fluorescent labels using a laser and confocal microscope, and enzyme labels by the action of an enzyme label on a substrate, typically to produce a colour change. In further embodiments, the developing agent is tagged to allow its detection, e.g. linked to a nucleotide sequence which can be amplified in a PCR reaction to detect the analyte. Other labels are known to those skilled in the art are discussed below. The developing agent(s) can be used in a competitive method in which the developing agent competes with the analyte for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte. In alternative embodiments, the analyte can be tagged before applying it to the support comprising the binding agent.

Pharmaceutical Uses

The antibodies of the invention can be formulated in compositions for diagnostic or therapeutic use. In this case, the antibodies are provided in an isolated and/or purified form and are typically present in the composition as at least about 90% active ingredient, more preferably at least about 95%, more preferably at least about 98%. Such a composition may, however, include inert carrier materials or other pharmaceutically and physiologically acceptable excipients. As noted below, a composition according to the present invention may include in addition to an antibody as disclosed, one or more other molecules of therapeutic use, such as an anti-tumour agent. In a preferred embodiment, the antibodies are linked to effectors which are anti-tumour drugs or prodrugs to target the effector to cells expressing CYP1B1.

An antibody of the invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, lactated Ringer's injection. Preservatives, stabilisers, buffers, antioxidants and/or other additives may be included, as required.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

The antibodies of the invention can be used to target therapy to cells or areas of the body where CYP1B1 is expressed. Targeting therapies may be used to deliver the active agent, either drugs or prodrugs, more specifically to cells expressing or displaying CYP1B1. Targeting may be desirable for a variety of reasons, for example if the agent is unacceptably toxic, or if it would otherwise require too high a dosage, or if it would not otherwise be able to enter the target cells. The agent may be administered in a precursor form, for conversion to the active form by an activating agent produced in, or targeted to, the cells to be treated. This type of approach is sometimes known as ADEPT, the former involving targeting the activating agent to the cells by conjugation to a cell-specific antibody of the invention.

EXPERIMENTAL

P450 Sequence Alignment, Peptide Selection and Immunisation

Based on a combination of structural homology modelling and sequence alignment of the human CYP1B1 amino acid sequence with the human CYP1A1 and CYP1A2 amino acid sequences a 148 amino acid segment located in the C-terminal third of the CYP1B1 protein was predicted to contain regions of amino acids which would be located on the external aspect of the CYP1B1 protein. Peptides of either 14 or 15 amino acid residues corresponding to this segment of the CYP1B1 protein were synthesised in the University of Aberdeen Protein Facility. The individual peptide sequences and amino acid location on the CYP1B1 protein are listed in Table 1. The right hand column indicates the peptide fragments which produced an immune reaction (peptides D and E).

TABLE 1

Peptide sequences and amino acid location on CYP1B1 protein of peptides used for immunisation

| | | | |
|---|---|---|---|
| A | NLPYVLAFLYEAMRF (SEQ ID NO. 6) | 377-391 | − |
| B | SSFVPVTIPHATTAN (SEQ ID NO. 7) | 392-406 | − |
| C | TSVLGYHIPKDTVVF (SEQ ID NO. 8) | 407-421 | − |
| D | VNQWSVNHDPVKWPN (SEQ ID NO. 1) | 422-436 | + |
| E | PENFDPARFLDKDGL (SEQ ID NO. 4) | 437-451 | + |
| F | INKDLTSRVMIFSVG (SEQ ID NO. 9) | 452-466 | − |
| G | KRRCIGEELSKMQLF (SEQ ID NO. 10) | 467-481 | − |
| H | LFISILAHQCDFRAN (SEQ ID NO. 11) | 482-496 | − |
| I | PNEPAKMNFSYGLT (SEQ ID NO. 12) | 497-510 | − |
| J | IKPKSFKVNVTLRE (SEQ ID NO. 13) | 511-524 | − |

Individual peptides were then conjugated to ovalbumin using glutaraldehyde as previously described (Duncan et al., 1992) and each peptide conjugate used as an immunogen. Individual peptide conjugates mixed with Freund's incomplete adjuvant were injected i.p into BALB/c mice and the mice were re-immunised with the same peptide conjugate 2-4 weeks following the initial immunisation. The presence of an immune response to each peptide conjugate was determined by testing serum (obtained 10 days after the second immunisation) from each mouse for recognition of expressed CYP1B1 by immunoblotting. The mice whose sera gave the best recognition of CYP1B1 were then given a final immunisation with the appropriate peptide conjugate and used for the production of monoclonal antibodies

Monoclonal Antibodies to CYP1B1

Four days after the final immunisation with peptide conjugate the mice were sacrificed, their spleens isolated and splenic cells fused with mouse myeloma cells (Ag8.653). The resultant hybridoma clones were then screened for antibody production by enzyme linked immunoassay (ELISA) using the relevant peptide conjugated with bovine serum albumin (BSA). The BSA conjugates were bound to an ELISA plate by incubation overnight at 4° C. in 50 mM sodium carbonate/bicarbonate buffer, pH 9.6, and the ELISA was performed as described previously (Duncan et al., 1992, Murray et al., 1998b). Hybridomas clones which were strongly positive by ELISA were subcloned twice and further tested by immunoblotting using expressed CYP1B1, expressed CYP1A1, control microsomes and human liver microsomes. The monoclonal antibodies were isotyped using an Isostrip kit (Roche Diagnostics, Lewes, Sussex, UK) which was performed according to the manufacturer's instructions.

Tissues

Samples of normal tissues (liver, kidney, lung, pancreas, adrenal cortex, brain, stomach, jejunum, colon, breast and ovary) were obtained from fresh, unfixed tissue samples submitted to the Department of Pathology, University of Aberdeen for diagnosis. Samples of tissue were frozen in liquid nitrogen and stored at −75° C. prior to preparation of microsomes. Samples of primary breast cancer (n=61) were obtained from samples of breast tissue submitted to the Department of Pathology, University of Aberdeen for diagnosis. All the samples of breast tissue were from needle core biopsies of palpable breast lumps performed as the diagnostic protocol prior to definitive treatment. The core biopsies were fixed in 10% neutral buffered formalin at room temperature and then routinely embedded in wax.

The diagnosis of breast cancer was performed with haematoxylin and eosin stained sections using standard histopathological criteria. The tumours were graded according to criteria described by Elston and Ellis (1991) and the estrogen receptor status of the breast cancers was assessed by immunohistochemistry for oestrogen receptor protein as previously described (King et al., 1997). The lymph node status was assessed from subsequent axillary lymph node samples submitted for histopathological examination. The clinico-pathological characteristics of the breast cancers are described in Table 2.

TABLE 2

Clinico-pathological characteristics of breast cancer

| | |
|---|---|
| Age (mean and range) | 52.3 years (34-76) |
| Histological type | |
| Invasive ductal carcinoma | 52 (85.2%) |
| Invasive lobular carcinoma | 8 (13.1%) |
| Tubulo-lobular carcinoma | 1 (1.7%) |
| Grade of breast cancer | |
| Grade 1 | 10 (16.4%) |
| Grade 2 | 27 (44.3%) |
| Grade 3 | 24 (39.3%) |
| Lymph node status | |
| negative (no metastasis) | 34 (55.7%) |
| positive (presence of metastasis) | 22 (36.1%) |
| not determined | 5 (8.2%) |
| Estrogen receptor status | |
| negative | 25 (41%) |
| positive | 34 (55.7%) |
| not determined | 2 (3.3%) |

Expressed CYP1B1 and CYP1A1

Microsomes prepared from human lymphoblastoid cells containing expressed human CYP1B1, expressed human CYP1A1 or control lymphoblastoid cells which only contained vector were obtained from Gentest Corp. Woburn, Ma.

Preparation of Microsomes

Frozen samples of tissues were thawed on ice in 0.01M Tris-HCl pH 7.4 containing 1.15% KCl. The thawed samples of tissue were dissected free of connective tissue and fat, finely chopped using a scalpel and then homogenised in 0.01M Tris-HCl containing 0.25M sucrose and 15% glycerol using a Polytron PT3000 homogeniser (Kinematica AG, Switzerland). The homogenates were then centrifuged at 15,000 g for twenty minutes at 4° C. using a Centrikon T-124 centrifuge (Kontron Instruments, Cumbernauld, UK). The resultant supernatants were then centrifuged at 180,000 g (44,000 rpm) for one hour at 4° C. using a Centrikon T-1160 centrifuge (Kontron Instruments). The pellet obtained after centrifugation was resuspended in 0.1M Tris-HCl containing 15% glycerol and 1 mM EDTA (Sigma-Aldrich Co. Poole, Dorset, UK) and centrifuged again at 180,000 g (44,000 rpm) for one hour at 4° C. The final microsomal pellet was re-suspended in 0.1M Tris-HCl containing 15% glycerol and 1 mM EDTA and the microsomal samples were then stored at −75° C. prior to use. The protein concentration of each sample of microsomes was determined using Bradford's method (Bradford, 1976). Bovine serum albumin (Sigma-Aldrich) was used as the protein standard.

Immunoblotting

Samples of microsomal proteins were electrophoretically separated at constant current in a 10% polyacrylamide gel using a Hoefer SE600 vertical gel electrophoresis apparatus (Amersham Pharmacia Biotech, Little Chalfont, Bucks, UK) and then transferred at constant current for 18 hours to nitrocellulose (Hybond ECL, Amersham Pharmacia Biotech) by electroblotting using a Hoefer TE42 blotting system (Amersham Pharmacia Biotech). After electrophoretic transfer non-specific protein binding sites were blocked by incubation of the nitrocellulose membrane for 60 minutes at room temperature in wash buffer consisting of 2% non-fat milk (Marvel, Premier Beverages, Stafford, UK) in 10 mM phosphate buffered saline containing 0.05% Tween 20 (Sigma). The nitrocellulose was then sequentially incubated with immune mouse serum (1/250) or CYP1B1 monoclonal antibody (1/100) and goat anti-mouse immunoglobulin conjugated to horseradish peroxidase (1/2000; Bio-Rad, Hemel Hempstead, UK). Following incubation with each antibody the membrane was washed for five 10 minute periods with wash buffer and after removal of unbound secondary antibody the membrane was further washed in 10 mM phosphate buffered saline for five 10 minute periods. Horseradish peroxidase was then demonstrated using an enhanced chemiluminescent technique (ECL plus, Amersham Pharmacia Biotech) which was performed as previously described (McKay et al., 1995; Murray et al., 1997). Briefly, the nitrocellulose membrane was incubated in a solution consisting of 4 ml of detection reagent 1 (lumigen PS-3, Amersham Pharmacia Biotech) and 100 µl of detection solution 2 (luminol PS-3, Amersham Pharmacia Biotech) for 5 minutes at room temperature, blotted dry, wrapped in clear plastic film and then exposed to X-ray film (Amersham Pharmacia Biotech).

Immunohistochemistry

Immunohistochemical detection of CYP1B1 was performed using a catalysed signal amplification method (King et al., 1997). In this study we used fluorescein tyramide rather than biotinylated tyramide which we had used in our previous study (King et al., 1997) to avoid any possible interference from endogenous biotin. Sections (4 µm in thickness) were cut onto aminoethyl propoxy 1 silane coated slides then dewaxed in xylene, rehydrated in 100% ethanol, 95% ethanol and washed in 0.05M Tris-HCl pH 7.6 containing 150 mM NaCl (TBS). Endogenous peroxidase was inhibited using a solution consisting of 90 ml methanol and 3 ml hydrogen peroxide. In some experiments antigen retrieval was performed by microwaving the sections in 0.01M citrate buffer pH6.0 for 20 minutes in microwave (Proline™, Proline, UK) operated at full power (800 W) while in other experiments no antigen retrieval was performed. After the antigen retrieval step sections were then allowed to cool to room 1 temperature and then the primary monoclonal anti-CYP1B1 antibody applied.

The primary antibody was applied as tissue culture supernatant at various dilutions (undiluted to 1/160) for 60 minutes at room temperature. After incubation in primary antibody the sections were washed in TBS for three successive 5 minute periods and then peroxidase conjugated rabbit anti-mouse immunoglobulin (1/100 in TBS containing 4% normal human serum, Dako, High Wycombe, UK) was applied for 30 minutes at room temperature. The sections were then washed in TBS and TBS containing 0.05% Tween 20 (TNT buffer). The sections were then further washed in TNT buffer and fluorescein tyramide (NEN, Hounslow, Middlesex, UK) applied for 10 minutes at room temperature. The sections were then further washed in TNT buffer followed by a application of monoclonal mouse anti-fluorescein (1/20, Dako) for 30 minutes at room temperature. Following further washing in TNT buffer peroxidase conjugated rabbit anti-mouse immunoglobulin (1/100 in TBS containing 4% normal human serum) was applied for 30 minutes at room temperature. After washing in TBS sites of bound peroxidase were then demonstrated calorimetrically using a solution containing diaminobenzidine and hydrogen peroxide (Liquid DAB plus, Dako). After incubating the sections for 10 minutes at room temperature in peroxidase substrate solution, the reaction was stopped by washing the slides in cold tap water and the enzyme reaction product was intensified using 0.5% copper sulphate. The slides were then washed in cold tap water, counterstained with haematoxylin, dehydrated in alcohol, cleared in xylene and mounted in a synthetic mounting media (DPX, BDH, Poole, Dorset, UK). The sections were examined using bright field light microscopy by two independent observers in order to establish the presence or absence of immunostaining, and its distribution and localisation and intensity. A tumour was regarded as positive if any tumour cells showed immunostaining while a tumour was classified as negative if there was a complete absence of immunostaining in tumour cells.

Positive control tissue was sections of a breast cancer which we have previously shown to contain CYP1B1 by both immunoblotting and immunohistochemistry with a polyclonal antibody to CYP1B1 (Murray et al., 1997). Negative controls used in place of the primary monoclonal antibody were TBS and tissue culture media. In one experiment antibody was liquid phase pre-absorbed with the peptide (peptide E, 10 nmol of peptide/ml antibody) which had been used as the immunogen for the monoclonal antibodies prior to performing immunohistochemistry.

Localisation of CYP1B1 in Ovarian Cancer

Immunohistochemical detection of CYP1B1 with a monoclonal antibody to CYP1B1 was performed using a tyramine signal amplification method. Sites of immunoreactivity were demonstrated calorimetrically with diaminobenzidine and hydrogen peroxide (Liquid DAB plus, Dako Ltd High Wycombe, Bucks, UK). Positive control tissue was sections of breast cancer which contain CYP1B1 and the negative control used Tris buffered saline (TBS) in place of the primary monoclonal antibody. To establish the presence or absence of CYP1B1 and its distribution, intensity and cellular localisation, the sections were examined using bright field light microscopy by two independent observers. CYP1B1 immunoreactivity in the tumours was assessed as strong, moderate, weak or negative. Tumours exhibiting CYP1B1 immunoreactivity in more than 5% of the cell were considered as positive.

Results

Development of monoclonal antibodies to CYP1B1 The immune response of sera from mice injected with each of the peptide conjugates was assessed by sodium dodecyl sulphate polyacrylamide gel electrophoresis and immunoblotting using expressed CYP1B1 as the antigen. The sera of mice injected with different peptides showed a variable immune response (Table 1 above). Sera of mice which had been injected with peptides D and E both showed recognition of CYP1B1 and were judged to have a produced a positive immune response. Sera from mice injected with peptide E gave a marginally stronger recognition of expressed human CYP1B1 than peptide D. However, sera from mice injected with peptides A and B and peptides F to J showed no apparent recognition of CYP1B1 and were considered to have produced no significant immune response. Mice which had been immunised with peptide E were therefore chosen to develop monoclonal antibodies to CYP1B1. The peptide sequence used to develop the monoclonal antibodies shows a high degree of similarity with corresponding rat CYP1B1 and mouse CYP1B1 sequences with 13 of the 15 amino acid residues being identical.

Peptide E

```
human CYP1B1    PENFDPARFLDKDGL (SEQ ID NO. 4)
rat CYP1B1      PEDFDPARFLDKDGF (SEQ ID NO. 3)
mouse CYCP1B1   PEDFDPARFLDKDGF (SEQ ID NO. 3)
                ** ***********
```

Amino acid residues common to all three P450s are indicated with an asterisk.

Figure 1:
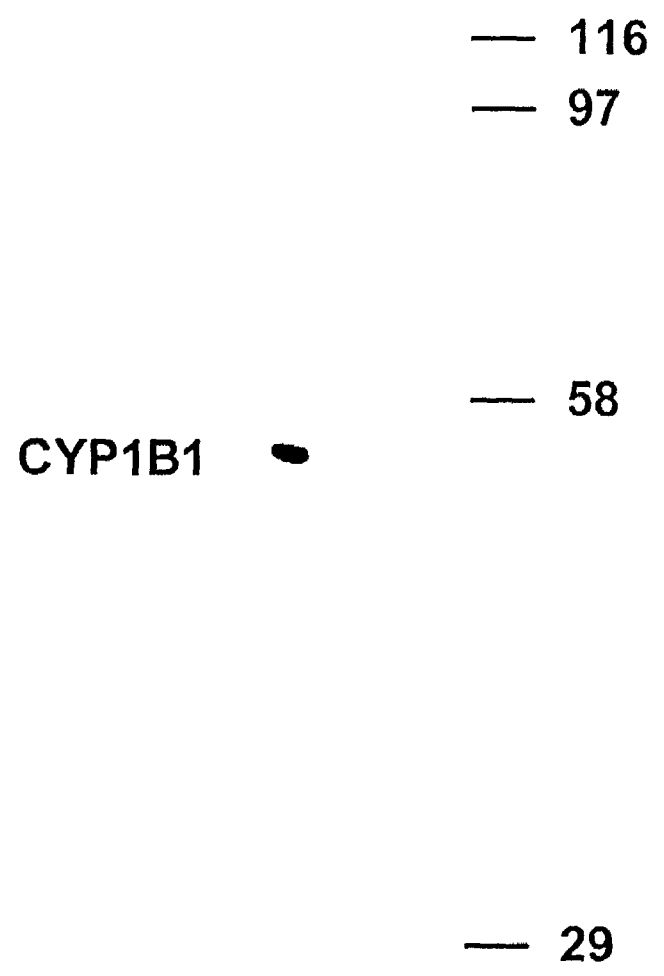
Figure 3:
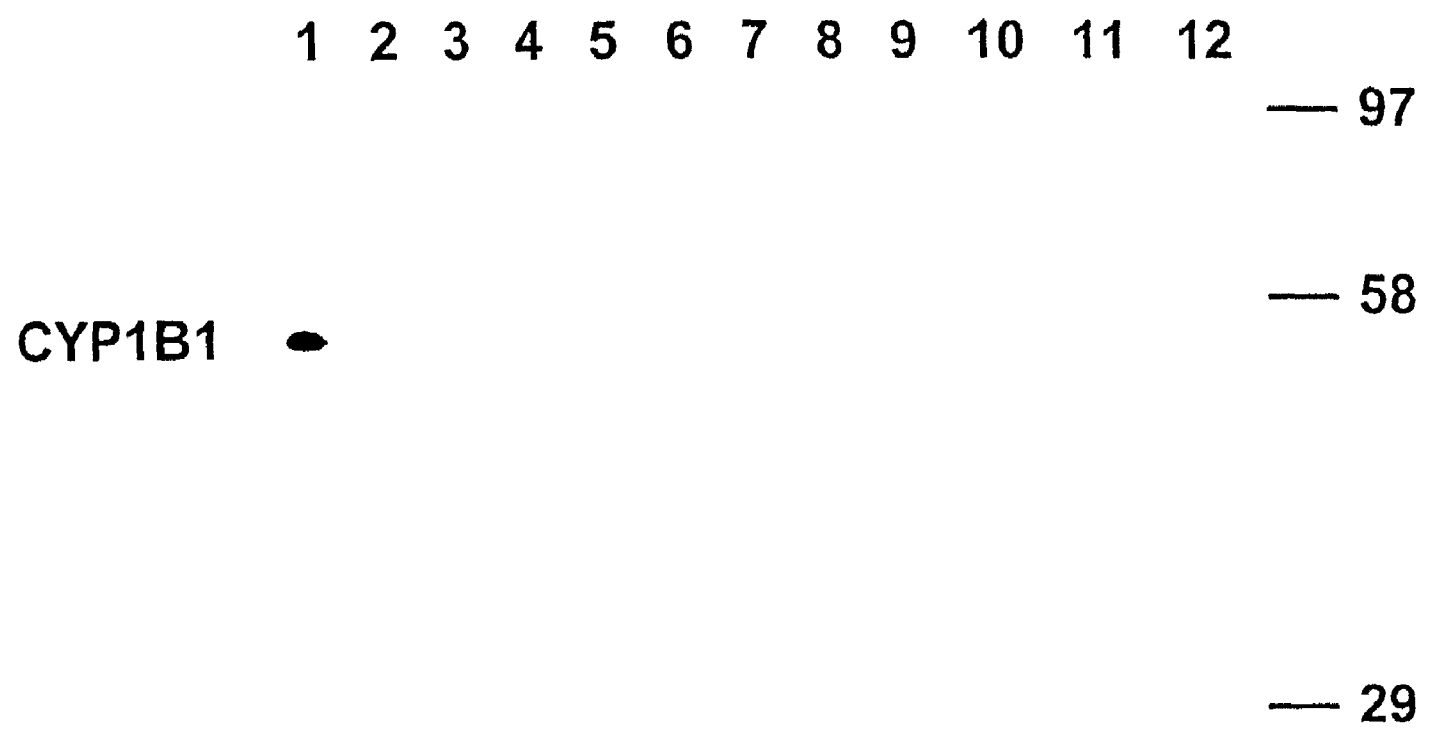

Five monoclonal antibodies were developed from mice immunised with peptide E. The individual antibodies were designated 5C4, 5D3, 5D9, 5E2 and 5G7 and isotyping showed that all the antibodies are IgG1κ subtype. All the monoclonal antibodies recognised a single immunoreactive band of molecular size 52 kDa corresponding to the expected molecular size of expressed human CYP1B1 by immunoblotting and did not recognise expressed human CYP1A1, or any protein present in vector only control microsomes or human liver microsomes (FIG. 1). Serial dilutions of expressed CYP1B1 indicated that the minimum detectable amount of CYP1B1 by immunoblotting was 0.05 pmol of expressed CYP1B1 (FIG. 2). CYP1B1 was not identified by immunoblotting microsomes prepared from a range of normal adult human tissues including kidney, stomach, small intestine, colon and lung (FIG. 3).

Immunohistochemistry on formalin fixed wax embedded sections of breast cancer used as the positive control showed that three of the monoclonal antibodies (5D3, 5E2 and 5G7) demonstrated strong staining while two of the antibodies (5C4, 5D9) showed no immunoreactivity. All the monoclonal antibodies which showed positive immunoreactivity required an antigen retrieval step for optimum immunohistochemical results and all three antibodies showed an identical pattern of localisation and distribution of immunohistochemical staining. Therefore only one of the monoclonal antibodies (5D3) was used for the subsequent immunohistochemical studies of breast cancer. Liquid phase pre-incubation of anti-CYP1B1 antibody with peptide E prior to performing immunohistochemistry almost completely abolished immunoreactivity.

CYP1B1 immunoreactivity was identified in 47 (77%) of cases of breast cancer while there was no detectable CYP1B1 immunoreactivity in 14 cases (23%). In each case in which there was CYP1B1 immunoreactivity the immunoreactivity was localised to the cytoplasm of tumour cells. The intensity of the immunoreactivity ranged from strong in 10 (16.4%) cases, moderate in 12 (19.7%) cases and weak immunoreactivity was present in 25 (41%) cases. The presence of CYP1B1 in different grades, histological types of breast cancer and lymph node status is summarised in Tables 3-5.

TABLE 3

The presence of CYP1B1 in different histological types of breast cancer

| CYP1B1 immunoreactivity | Histological type of breast cancer | | |
|---|---|---|---|
| | Invasive Ductal (n = 52) | Invasive lobular (n = 8) | Tubulo-lobular (n = 1) |
| Negative (n = 14) | 12 | 2 | 0 |
| Weak (n = 25) | 20 | 4 | 1 |
| Moderate (n = 12) | 11 | 1 | 0 |
| Strong (n = 10) | 9 | 1 | 0 |

TABLE 4

Comparison of CYP1B1 with different grades of breast cancer

| CYP1B1 immunoreactivity | Grade of breast cancer | | |
|---|---|---|---|
| | Grade 1 (n = 10) | Grade 2 (n = 27) | Grade 3 (n = 24) |
| Negative (n = 14) | 2 | 6 | 6 |
| Weak (n = 25) | 4 | 12 | 9 |
| Moderate (n = 12) | 3 | 5 | 4 |
| Strong (n = 10) | 1 | 4 | 5 |

TABLE 5

Comparison of CYP1B1 in lymph node positive and lymph node negative breast cancer cases

| CYP1B1 immunoreactivity | Lymph node status | |
|---|---|---|
| | Lymph node positive (n = 34) | Lymph node negative (n = 22) |
| Negative (n = 14) | 6 | 8 |
| Weak (n = 24) | 16 | 8 |
| Moderate (n = 11) | 6 | 5 |
| Strong (n = 7) | 6 | 1 |

There was no CYP1B1 immunoreactivity in stromal cells or connective tissue nor in the following cell types including lymphocytes and plasma cells when they were present in individual biopsies. The presence of CYP1B1 was associated with the presence of estrogen receptor protein (Table 6, $\chi^2=8.54$; p=0.03) while there was no relationship between the presence of CYP1B1 and the histological type of the tumour, tumour grade or the presence or absence of lymph node metastasis.

TABLE 6

Correlation of the presence of CYP1B1 immunoreactivity in breast cancer with the presence of estrogen receptor ($\chi^2 = 8.54$; p = 0.03)

| CYP1B1 immunoreactivity | Estrogen receptor status | |
| --- | --- | --- |
| | Negative (n = 25) | Positive (n = 34) |
| Negative (n = 13) | 2 | 11 |
| Weak (n = 25) | 14 | 11 |
| Moderate (n = 12) | 7 | 5 |
| Strong (n = 9) | 2 | 7 |

CYP1B1 Expression in Primary Colorectal Cancer

The antibodies were then used to investigate CYCP1B1 expression in 80 primary colorectal cancers and 14 liver metastases from primary colorectal cancer. Of 14 liver metastases tested 13 showed expression of CYP1B1.

| | Frequency | Percent | Valid Percent | Cumulative Percent |
| --- | --- | --- | --- | --- |
| Valid 0.00 | 11 | 13.8 | 13.8 | 13.8 |
| 1 | 4 | 5 | 5 | 18.8 |
| 2 | 28 | 35 | 35 | 53.8 |
| 3 | 37 | 46.3 | 46.3 | 100 |
| Total | 80 | 100 | 100 | |
| Total | 80 | 100 | | |

| Case | Intensity | Percentage CYP1B1 Positive Cells |
| --- | --- | --- |
| 1 | | 0 |
| 2 | 1 | >75% |
| 3 | 2 | 50-75% |
| 4 | 3 | >75% |
| 5 | 2 | 50-75% |
| 6 | 3 | 25-50% |
| 7 | 3 | 50-75% |
| 8 | 3 | >75% |
| 9 | 3 | >75% |
| 10 | 3 | >75% |
| 11 | 1 | 25-50% |
| 12 | 3 | 50-75% |
| 13 | 3 | >75% |
| 14 | 3 | >75% |

Localisation of CYP1B1 in Ovarian Cancer

CYP1B1 immunoreactivity was identified in the majority (153/167; 92%) of primary ovarian cancer sections and was specifically localised to the cytoplasm of tumour cells. There was no detectable CYP1B1 expression in any of the normal ovarian tissue samples. In a high percentage of the ovarian cancers there was either strong (85/167; 50.9%) or moderate (39/167; 23.4%) immunoreactivity for CYP1B1. In addition, the presence of CYP1B1 was observed in the majority (45/48; 94%) of metastatic deposits with a high proportion showing moderate (22/48; 45.8%) to strong (18/48; 37.5%) immunoreactivity. A similar level of CYP1B1 expression was exhibited for the different histological subtypes in both primary and metastatic tumour. In the cases where both primary ovarian tumour and metastatic deposits were available, a significant correlation for CYP1B1 expression (p=0.02 Spearman correlation test) was observed.

Discussion

CYP1B1 shows increased expression in a variety of tumours including breast cancer (Murray et al. 1997) and there is elevated CYP1B1 associated 4-estradiol hydroxylase activity in breast cancer (Liehr and Ricci et al., 1996). CYP1B1 is also capable of metabolizing a variety of putative human carcinogens including polycyclic aromatic hydrocarbons and heterocyclic amines (Shimada et al., 1996; Crespi et al., 1997). Thus CYP1B1 appears to have potentially important roles in tumour development and progression, as a potential target for anti-cancer drugs and as a tumour biomarker. The initial studies of the presence of CYP1B1 in individual types of tumours were performed with a polyclonal antibody to CYP1B1 and for each tumour type only a small number of tumour samples were investigated (Murray et al., 1997). To evaluate more fully the potential of CYP1B1 (tumour development and progression) as a tumour marker required monoclonal antibodies disclosed herein that specifically recognise CYP1B1 in formalin fixed wax embedded tissue sections and also requires a larger number of tumours to be studied. The present work describes the development of such monoclonal antibodies to CYP1B1, and demonstrates that they sensitively and specifically detect CYP1B1 by immunoblotting and immunohistochemistry and then uses these antibodies to investigate the presence of CYP1B1 in a series of primary breast cancers, prostate cancer and ovarian cancer.

The strategy used to develop monoclonal antibodies to CYP1B1 was a combination of structural molecular modelling and sequence alignment to identify regions of CYP1B1 which were likely to be located on the external aspect of the CYP1B1 protein and thus likely to be immunogenic. A region located in the C-terminal third of the CYP1B1 protein encompassing the haem binding region was identified and peptides consisting of either 14 or 15 amino acid residues were synthesised and conjugated to carrier protein. Each peptide was injected into mice and the immunoreactivity of each peptide for CYP1B1 was assessed by immunoblotting using microsomes prepared from human lymphoblastoid cells containing expressed CYP1B1 and microsomes containing vector only. Only sera from mice immunised with peptides D and E showed recognition of CYP1B1 whereas none of the other peptides showed significant immunoreactivity for CYP1B1. Mice which had been immunised with peptide E were selected for the development of monoclonal antibodies to CYP1B1. The peptide sequence used for the generation of the monoclonal antibodies shows a high degree of similarity (13 out of 15 amino acids identical) with rat CYP1B1 and mouse CYP1B1 and it would be anticipated that the monoclonal antibodies would also recognise rat CYP1B1 and mouse CYP1B1. All the monoclonal antibodies were specific for CYP1B1 and did not recognise either CYP1A1 or CYP1A2 the other known members of the CYP1 gene family. Furthermore the antibodies did not recognise any other protein in human liver microsomes. Human liver microsomes were used as a source for CYP1A2 as CYP1A2 is one of the major forms of P450 constitutively expressed in liver and liver microsomes also acted as a source for several other forms of P450 thus providing a broad screen to confirm the specificity of the antibodies for CYP1B1.

The present study was unable to detect CYP1B1 by immunoblotting in a range of normal human tissues. The absence of CYP1B1 protein in both normal human liver and a range of extra-hepatic tissues is consistent with the previous immunohistochemical studies (Murray et al., 1997) in that CYP1B1 protein was not detected. In this study, a relatively high amount of microsomal protein (30 µg) was loaded per lane and a highly sensitive chemiluminescent detection system was used so it seems likely that even a very low level of CYP1B1 in the normal tissues studied would have been detected using this system.

A further major aim of this study was to develop antibodies to CYP1B1 which could be used in immunohistochemistry and that were effective on formalin fixed wax embedded sections of tissue. All the monoclonal antibodies were evaluated by immunohistochemistry using formalin fixed wax embedded sections of breast cancer which have previously been shown by immunoblotting to contain a relatively high level CYP1B1 (Murray et al., 1997) and three of the monoclonal antibodies were found to detect effectively CYP1B1 by immunohistochemistry. Since the three antibodies that gave positive immunoreactivity all produced an identical pattern and intensity of immunoreactivity, only one of the antibodies was used to investigate CYP1B1 expression.

The present study found that 77% of breast cancers contained CYP1B1 and in each tumour CYP1B1 was specifically localised to tumour cells. The high frequency of expression of CYP1B1 in breast cancer is very similar to previous studies of a small number of breast cancers and would support the concept that CYP1B1 is a major form of cytochrome P450 present in breast cancer (McKay et al., 1995; Murray et al., 1997). CYP1B1 was found in all histological types of breast cancer and the presence of CYP1B1 was not associated with any particular histological type of breast cancer nor the presence or absence of lymph node metastases, however the expression of CYP1B1 did correlate with the presence of estrogen receptor protein. This is of interest as recently an association between a CYP1B1 polymorphism (valine/leucine) at amino acid 432 and estrogen receptor status in breast cancer has been described (Bailey et al., 1998). There is also the potential for "cross talk" between the estrogen receptor complex and the aryl hydrocarbon receptor complex (Wang et al., 1998) which is involved in the transcriptional regulation of CYP1B1 (Schmidt and Bradfield, 1996).

Since CYP1B1 is involved in estrogen metabolism acting as a specific C4 hydroxylase of estradiol (Hayes et al., 1996) then the presence of CYP1B1 in breast cancer cells is likely to make a significant contribution to the intra-tumoural metabolism of estradiol. The presence of CYP1B1 in breast cancer also provides a molecular target for drugs specifically activated by CYP1B1.

The development of monoclonal antibodies to CYP1B1 that are effective in formalin fixed wax embedded sections should make them useful for investigating CYP1B1 expression in different tumour types and related pre-neoplastic lesions. The antibodies can be used for the diagnosis of cancer. The antibodies can also be developed as the basis of immunochemical in vivo diagnostic tests and as therapeutics targeted to the CYP1B1 protein or a degradation product thereof.

REFERENCES

The references cited herein are expressly incorporated by reference.

Bailey et al, Cancer Res., 58:5038-5041, 1998.
Bhattacharyya et al, J. Biol. Chem., 270:11595-11602, 1995.
Crespi et al, Carcinogenesis, 12:83-89, 1997.
Duncan et al, J. Immunol. Meth., 151:227-236, 1992.
Elston & Ellis, Histopathology, 19:403-410, 1991.
Hakkola et al, Carcinogenesis, 18:391-397, 1997.
Hayes et al, P.N.A.S USA, 93:9776-9781, 1996.
King et al, J. Pathol., 183:237-241, 1997.
Liehr & Ricci, P.N.A.S. USA, 93:3294-3296, 1996.
McKay et al, FEBS Letters, 374:270-272, 1995.
Murray et al, J. Pathol., 185:256-261, 1998a.
Murray et al, Gut, 43:791-797, 1998b.
Murray et al, Cancer Res., 57:3026-3031, 1997.
Savas et al, J. Biol. Chem., 269:14905-14911, 1994.
Savas et al, Arch. Biochem. Biophys., 347:181-192, 1997.
Schmidt & Bradfield, Annu. Rev. Cell Dev. Biol.,
Shen et al, DNA Cell Biol., 13:763-769, 1994.
Shimada et al, Cancer Res., 56:2979-2984, 1996.
Sutter et al, J. Biol. Chem., 269:13092-13099, 1994.
Tang et al, J. Biol. Chem., 271:28324-28330, 1996.
Walker et al, Carcinogenesis, 16:1319-1327, 1995.
Wang et al, Nucl. Acid. Res., 26:3044-3052, 1998.

The invention claimed is:

1. A method of making an antibody that specifically binds to cytochrome P450 CYP1B1, the method comprising raising the antibody using a peptide consisting of an amino acid sequence VNQWSVNHDPVKWPN (SEQ ID NO: 1) or PExFDPARFLDKDGy, where x is D or N and y is L or F (SEQ ID NOs 2 to 5), or an antigenic fragment thereof.

2. The method of claim 1, wherein the peptide consists of 3 to 10 amino acids.

3. The method of claim 1, wherein the peptide consists of 3 to 6 amino acids.

4. The method of claim 1, wherein the peptide is conjugated to an immunogenic carrier.

5. The method of any one of the preceding claims, wherein the antibody is a monoclonal antibody.

6. The method of claim 5, wherein the monoclonal antibody is as obtainable by a method which comprises:

(a) immunising an animal with the peptide conjugated to an immunogenic carrier;

(b) sacrificing the animal and fusing spleen cells obtained from the animal with myeloma cells to produce one or more hydridomas; and, (c) screening the hybridomas for antibodies capable of binding the peptide.

7. A method of producing an antibody having obtained a hybridoma by the method of claim 6, the method comprising culturing a hybridoma found in step (c) and isolating the antibody thus produced.

8. The method of claim 7, further comprising conjugating the antibody to an effector.

9. The method of claim 8, wherein the effector is a label, a toxin, a drug or prodrug, an enzyme or a transport molecule.

10. An isolated monoclonal antibody which is capable of specifically binding to cytochrome P450 CYP1B1, wherein the monoclonal antibody recognises an epitope in the cytochrome P450 CYP1B1 protein included within the amino acid sequence VNQWSVNHDPVKWPN (SEQ ID NO: 1) or PExFDPARFLDKDGy, where x is D or N and y is L or F (SEQ ID NOs: 2 to 5).

11. The antibody of claim 10, wherein the antibody recognises an epitope of between 3 and 10 amino acids from the amino acid sequences.

12. The antibody of claim 10, wherein the antibody recognises an epitope of between 3 and 6 amino acids from the amino acid sequences.

13. The antibody of claim 10 which is humanised.

14. The antibody of claim 10, wherein the antibody is obtainable by:

(a) immunising an animal with a peptide comprising the amino acid sequence VNQWSVNHDPVKWPN (SEQ ID NO: 1) or PExFDPARFLDKDGy, where x is D or N and y is L or F (SEQ ID NOs: 2 to 5), which peptide is conjugated to an immunogenic carrier;

(b) sacrificing the animal and fusing spleen cells obtained from the animal with myeloma cells to produce one or more hydridomas; and, (c) screening the hybridomas for antibodies capable of binding the peptide.

15. The antibody of claim 10, wherein the antibody is conjugated to an effector.

16. The antibody of claim 15, wherein the effector is a label, a toxin, a drug or prodrug, an enzyme or a transport molecule.

* * * * *